United States Patent
Bakai et al.

(10) Patent No.: US 7,466,792 B2
(45) Date of Patent: Dec. 16, 2008

(54) SYSTEM FOR PRODUCING CT IMAGE DATA RECORDS AND FOR IRRADIATING A TUMOR PATIENT

(75) Inventors: Annemarie Bakai, Erlangen (DE); Dieter Cherek, Hirschaid (DE); Joachim Grottel, Lauf (DE); Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 207 days.

(21) Appl. No.: 11/406,387

(22) Filed: Apr. 19, 2006

(65) Prior Publication Data

US 2006/0245537 A1    Nov. 2, 2006

(30) Foreign Application Priority Data

Apr. 20, 2005    (DE) .................. 10 2005 018 330

(51) Int. Cl.
  *A61B 6/03*    (2006.01)
  *A61N 5/10*    (2006.01)
(52) U.S. Cl. ........................... 378/16; 378/65
(58) Field of Classification Search ............. 378/65, 378/16
  See application file for complete search history.

(56) References Cited

U.S. PATENT DOCUMENTS

| | | | | |
|---|---|---|---|---|
| 4,998,268 | A * | 3/1991 | Winter | 378/65 |
| 5,008,907 | A * | 4/1991 | Norman et al. | 378/65 |
| 5,471,516 | A * | 11/1995 | Nunan | 378/65 |
| 5,751,781 | A * | 5/1998 | Brown et al. | 378/65 |
| 6,366,801 | B1 | 4/2002 | Cash, Jr. et al. | |
| 6,381,304 | B1 * | 4/2002 | Shoenfeld et al. | 378/65 |
| 6,385,286 | B1 * | 5/2002 | Fitchard et al. | 378/65 |
| 6,393,096 | B1 * | 5/2002 | Carol et al. | 378/65 |
| 6,501,828 | B1 | 12/2002 | Popescu | |

(Continued)

FOREIGN PATENT DOCUMENTS

DE    199 50 794 A1    6/2001

(Continued)

OTHER PUBLICATIONS

Robar et al., Tumour dose enhancement using modified megavoltage photon beams and contrast media, Physics in Medicine and Biology, 2002, vol. 47, pp. 2433-2449.*

*Primary Examiner*—Chih-Cheng G Kao
(74) *Attorney, Agent, or Firm*—Harness, Dickey & Pierce, P.L.C.

(57) ABSTRACT

A system includes exactly one rotary frame for holding at least one x-ray tube, and one radiation detector that is situated opposite, the x-ray tube being equipped with a diaphragm that can be dynamically adjusted. The system includes a first operating mode for imaging in which the x-ray tube radiate a ray fan of constant fan angle onto the oppositely situated detector, and CT image data records are calculated from the measured data of the detector. It includes a second operating mode for irradiation in which by using at least one imaging x-ray tube used in the first operating mode radiates an x-ray fan that varies with reference to alignment during the rotation of the rotary frame, is narrower perpendicular to the system axis, and remains aligned with the site of at least one tumor in the patient independently of the angular position of the rotary frame.

15 Claims, 4 Drawing Sheets

U.S. PATENT DOCUMENTS

| | | | |
|---|---|---|---|
| 6,661,866 B1 * | 12/2003 | Limkeman et al. | 378/4 |
| 6,990,175 B2 * | 1/2006 | Nakashima et al. | 378/65 |
| 6,999,556 B2 * | 2/2006 | Nakano | 378/65 |
| 2003/0003054 A1 | 1/2003 | McDonald et al. | |
| 2003/0048868 A1 | 3/2003 | Bailey et al. | |
| 2006/0153330 A1 * | 7/2006 | Wong et al. | 378/65 |

FOREIGN PATENT DOCUMENTS

| | | |
|---|---|---|
| EP | 0 382 560 A1 | 8/1990 |
| WO | WO 96/11023 | 4/1996 |
| WO | WO 00/69473 | 11/2000 |

* cited by examiner

SYSTEM FOR PRODUCING CT IMAGE DATA RECORDS AND FOR IRRADIATING A TUMOR PATIENT

The present application hereby claims priority under 35 U.S.C. §119 on German patent application number DE 10 2005 018 330.1 filed Apr. 20, 2005, the entire contents of which is hereby incorporated herein by reference.

FIELD

The invention generally relates to a system for producing CT image data records in a first operating mode, to an automatic irradiation plan and to a second operating mode for irradiating a tumor patient with the aid of an x-ray source.

BACKGROUND

Systems for combined CT imaging and therapeutic irradiation of patients are disclosed, for example, in patent application US 2003/0048868 A1. This patent application discloses a combined therapeutic irradiation and imaging system that on the one hand has a CT scanner with at least one x-ray tube and a detector situated opposite, the x-ray tube and the detector being fastened on a rotary frame (=gantry) and revolving in a fashion rotating thereabout for the purpose of scanning a patient while the patient is being pushed through the scanning area along the system axis by a displaceable patient couch. In addition, a separate irradiation apparatus, which serves for irradiating the patient therapeutically, is provided outside the gantry, but in the scanning plane of the gantry. The patient can thereby be scanned by the CT scanner without changing position, and subsequently be exposed directly to therapeutic irradiation without needing to be moved.

A device comparable thereto is known from the "Tomo-Therapy" company; it includes a conventional CT unit that is supplemented by an additional linear accelerator for therapeutic irradiation such that there is no need here either to reposition the patient between the scanning process and the irradiation.

Such devices are very expensive to manufacture and require a large amount of space owing to the combination of two basic units, and for this reason their market penetration has so far been slight.

SUMMARY

It is an object of at least one embodiment of the invention to find a system for producing CT image data records and for irradiating a tumor patient that is of less complex design and can therefore be manufactured more advantageously.

The inventors have realized that it is also possible to carry out therapeutic measures based on a CT scanner that is conventional per se, there being a need for this purpose to use a variable diaphragm setting such as described, for example, in laid-open patent application DE 199 50 794 A1. It is necessary for this purpose to equip the system with two different operating modes, a first operating mode serving for producing images, the tumor subsequently being detected in the arithmetic logic unit on the basis of the calculated volume display of the patient, and an irradiation plan automatically being carried out taking account of the structure of the patient, and the therapeutic irradiation subsequently being executed with the aid of the calculated irradiation plan in the second operating mode by using the same x-ray tube.

In addition, such a tumor detection and subsequent irradiation can be backed up with the aid of contrast agents or a device/method for sensitizing the tumor to radiation.

In accordance with this basic idea, in at least one embodiment the inventors propose an improved system for producing CT image data records and for irradiating a tumor patient, comprising:

exactly one rotary frame for holding at least one radiation source, and at least one radiation detector that is situated opposite and moves about a system axis, at least one x-ray tube as radiation source with a diaphragm that can be adjusted dynamically during rotation of the rotary frame, at least one detector with a multiplicity of detector elements, arranged in planar fashion, for measuring the radiation emanating the x-ray tube;

an arithmetic logic and control unit, a first operating mode for imaging, in which during the revolution of the rotary frame the at least one x-ray tube radiates a ray fan of constant fan angle onto the oppositely situated detector, and CT image data records are calculated from the measured data of the detector, and a second operating mode for irradiation, in which at least one x-ray tube used for imaging radiates an x-ray fan that varies with reference to alignment during the rotation of the rotary frame, is narrower perpendicular to the system axis, and remains aligned with the site of the at least one tumor in the patient independently of the angular position of the rotary frame.

As already mentioned, the patient can additionally be administered tumor-specific contrast media or a device/method for increasing the sensitivity to ionizing radiation. Reference may be made by way of example to the following documents with reference to the media: WO 2000 69473 A2, WO 96 11023 A1 and US 2003/003054 A1, the entire contents of each of which is hereby incorporated herein by reference.

According to at least one embodiment of the invention, the movement of the ray fan in the second operating mode is performed by continuous diaphragm adjustment. It is thereby possible to vary the direction of the beam during rotation of the gantry such that the therapeutic beam remains aligned exclusively with the tumor even in the case of an eccentrically seated tumor.

In an improved variant, the width of the ray fan is also additionally set during the irradiation such that the at least one tumor, which can appear to be narrower or wider in the projection depending on the current perspective of the therapeutic beam, can be hit in a more selected fashion by way of an appropriate beamwidth adaptation.

A further possibility for improving the selective dose application in the tumor tissue can be achieved by virtue of the fact that the accelerating voltage is varied during a rotation in the second operating mode. Owing to this variation in the accelerating voltage, there is also a change in the depth of penetration and the depth of the maximum deposition of energy, such that the latter can be adapted to the position of the at least one tumor in relation to the patient, and to the path actually covered by the beam through the patient. In this way, as soon as the path through the healthy tissue of the patient is shorter there is a reduction in the x-ray energy of the beam such that the depth of penetration of the beam is relatively slight, and the maximum deposition of energy takes place at the center of the tumor.

If, owing to the rotation of the gantry, the beam moves to the other side of the patient such that a longer path through healthy tissue must be covered before the tumor is reached, the accelerating voltage is increased. This results in enlargement of the depth of penetration while, at the same time, there is a reduction in the energy deposited in the healthy tissue. The aim is to make the setting in such a way that the maximum deposition of energy should also take place there at the center of the tumor.

On the basis of the known absorption coefficients, it is relatively easy to use the previously determined CT volume data to define in the irradiation plan which radiation energies must be used at which gantry angles, that is to say at which irradiation angles, in order to achieve optimum success. The accelerating voltage can be varied correspondingly during the revolution of the gantry.

In addition to this measure, or else as an independent one, the radiation energy applied can also be varied by using a spectral pre-filter such that it is thereby additionally possible to adapt the energy spectrum to the desired depth of penetration on the basis of the position of the tumor in the patient.

In addition, the dose rate can be varied in the second operating mode in order to avoid excessively large depositions of energy in the healthy tissue during rotation of the gantry. The dose rate can be varied either by varying the tube current, or by changing the pulse width in the case of a pulsed tube current.

Since the anode load for therapeutic irradiation is relatively high, as a rule, it can be advantageous to make use on the anode of the x-ray tube during the first operating mode a smaller focal spot that ultimately leads to very good imaging, whereas it is possible to make use in the second operating mode of a larger focal spot that loads the anode material less, the somewhat less sharp beam path being less crucial because of the widened focal spot in the region of the therapeutic irradiation.

It is also within the scope of at least one embodiment of the invention if a further x-ray tube is fitted on the gantry instead of a single x-ray tube. On the one hand, this further x-ray tube can be used in conjunction with an appropriate detector for the purpose of faster and improved imaging. However, it is also possible to design this second x-ray tube exclusively as an additional therapeutic radiation source in order to reduce the irradiation period during therapy.

In the case of this tube, as well, it is possible to provide a variable diaphragm control, or to use control of the accelerating voltage, to use spectral filters and/or to use dose rate variation. Again, the second irradiation source can be aligned with the variable diaphragm control for the purpose of simultaneous irradiation of a further tumor in the same irradiation plane such that two tumors at different locations and in the same radiation plane are simultaneously irradiated in parallel.

In addition, a PET or SPECT detector can additionally be used in supplementary fashion on the rotary frame in order thereby to improve the localization of a tumor in combination with the computed tomography imaging.

With reference to the concrete operating cycle between CT imaging and therapeutic irradiation, the inventors propose, on the one hand, that there be present for the system an operating program that moves the patient relative to the rotary frame sequentially in the direction of the system axis, image evaluation and automatic detection of the position of the at least one tumor taking place in the first operating state at each sequential position of the system axis, subsequently an automatic irradiation plan is carried out over the measured section with the aid of the measured structure of the patient, and thereupon in the second operating mode the at least one tumor is irradiated with the aid of the calculated irradiation data for the scanned section.

Thus, in this variant the patient is scanned in the area of the putative tumor and if a tumor is detected in this area an irradiation plan is automatically carried out over this area and irradiation is firstly performed in this plane on the basis of the irradiation plan carried out, this being done without feeding in the z-direction. Thereafter, feeding takes place in the direction of the system axis such that a new cross section of the patient is present in the scanning area and therapy area of the system, and the method is continued iteratively until the entire tumor has been irradiated and no further tumor is found in the pictorial illustration.

A further possibility resides in that there is present in the system an operating program that in the first operating state moves the patient continuously in the direction of the system axis relative to the rotary frame and carries out a complete spiral scan, image evaluation and automatic detection of the position of the at least one tumor then taking place. Subsequently an automatic irradiation plan is carried out with the aid of the measured structure of the patient, and thereupon in the second operating mode the at least one tumor is continuously irradiated with the aid of the calculated irradiation data.

In the case of both modes of procedure, there is no need to move the patient between the CT scan and the therapeutic irradiation, and so the localized tumor is also located at the intended location during the irradiation with a high degree of locational reliability. However, the reliability seems to be somewhat less with reference to a movement error of the patient during the examination or an interim repositioning by comparison with the method illustrated previously.

It is further possible for there to be present an operating program that during the therapeutic use of the radiation measures the absorption of this radiation in parallel on the detector and detects a movement of the tumor that may be present from the measured data. This can be done, for example, in the manner of a kymogram, or parallel images can be reconstructed and the tumor movement can be detected from the tomograms obtained. When this information is present, an operating program which uses the currently detected movement of the tumor for the immediate correction of the diaphragm setting and/or of the remaining irradiation parameters such as, for example, voltage or dose rate to additionally be present.

BRIEF DESCRIPTION OF THE DRAWINGS

Additional features and advantages of the invention can ensue from the following description of example embodiments with reference to the drawings, only the features required to understand the invention being illustrated.

The embodiments of the invention are to be explained below in more detail with the aid of the drawings, the following reference symbols being used: 1: CT irradiation therapy system; 2: x-ray tube; 2.1: focal spot; 2.2: diaphragm; 3: detector; 4: system axis; 5: housing; 6: displaceable patient couch; 7: patient; 7.1: tumor; 8: opening in the gantry; 9: arithmetic logic and control unit; 10: data and control line; 11: rotary frame; 12: detection module; 13: control module; 14: reconstruction module; 15: planning module; 16: ray fan; 17: detection module; d: depth of penetration; $Prg_1$-$Prg_n$: programs; $U_x$: accelerating voltage; $\phi$: fan angle.

Figure 1:
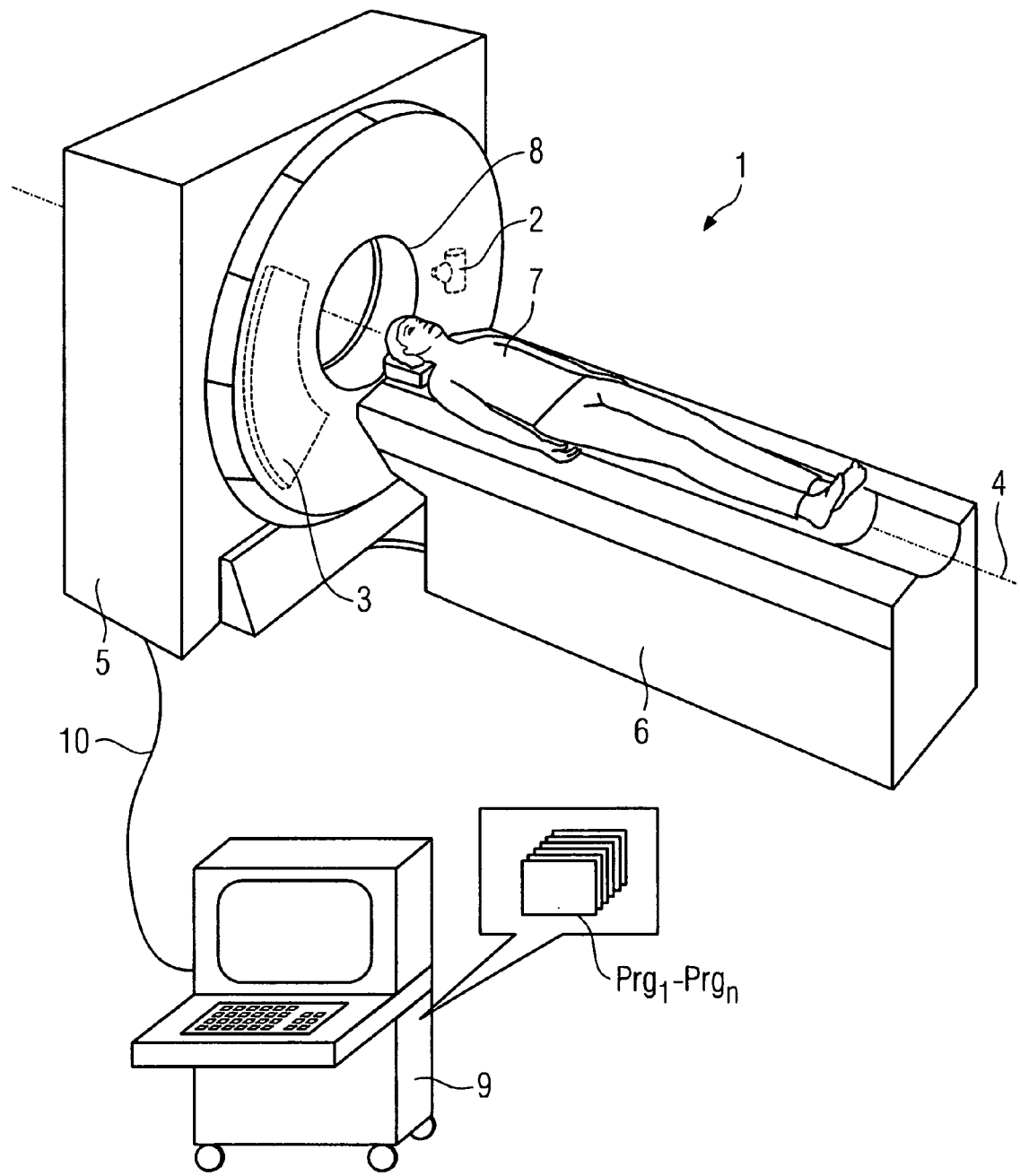
Figure 2:
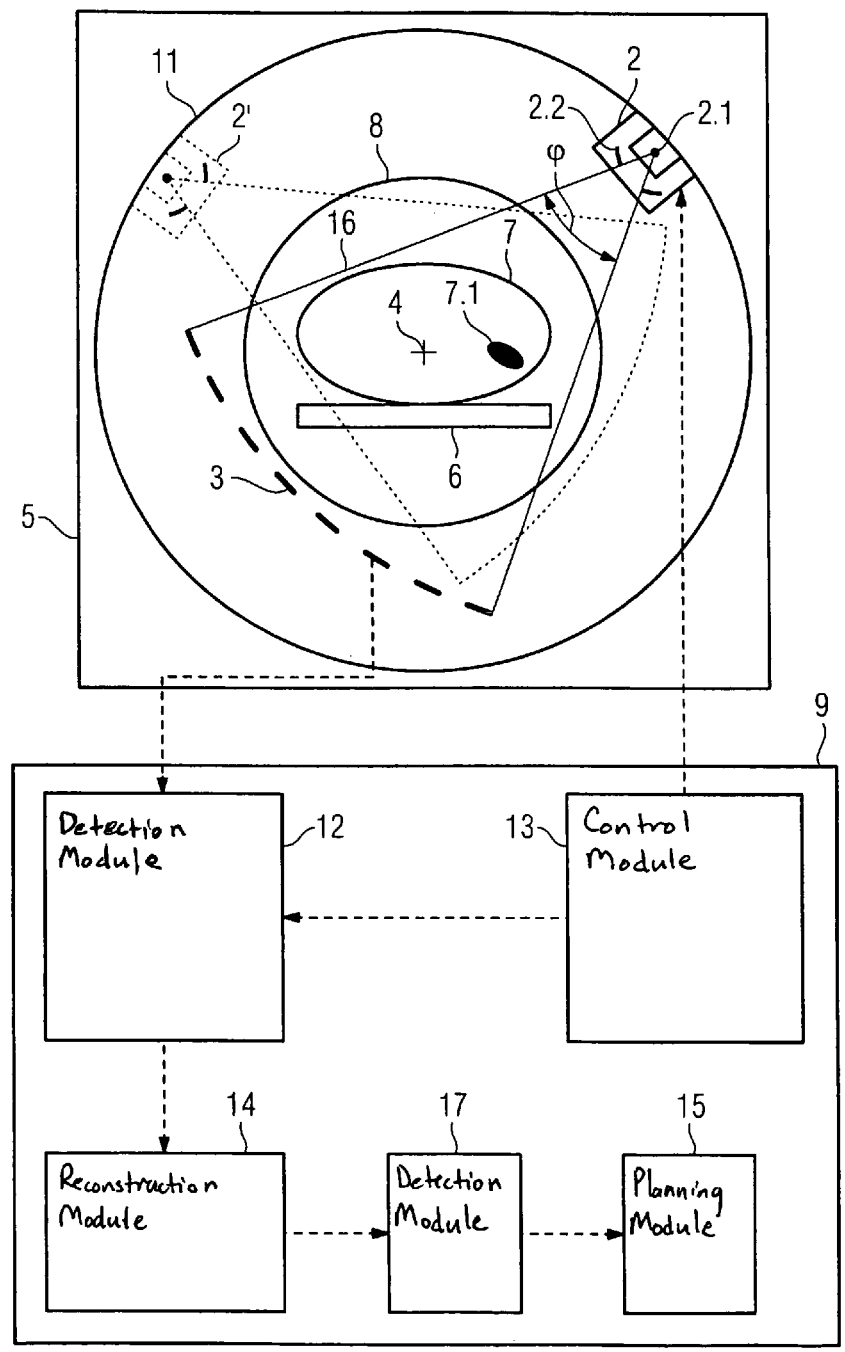
Figure 3:
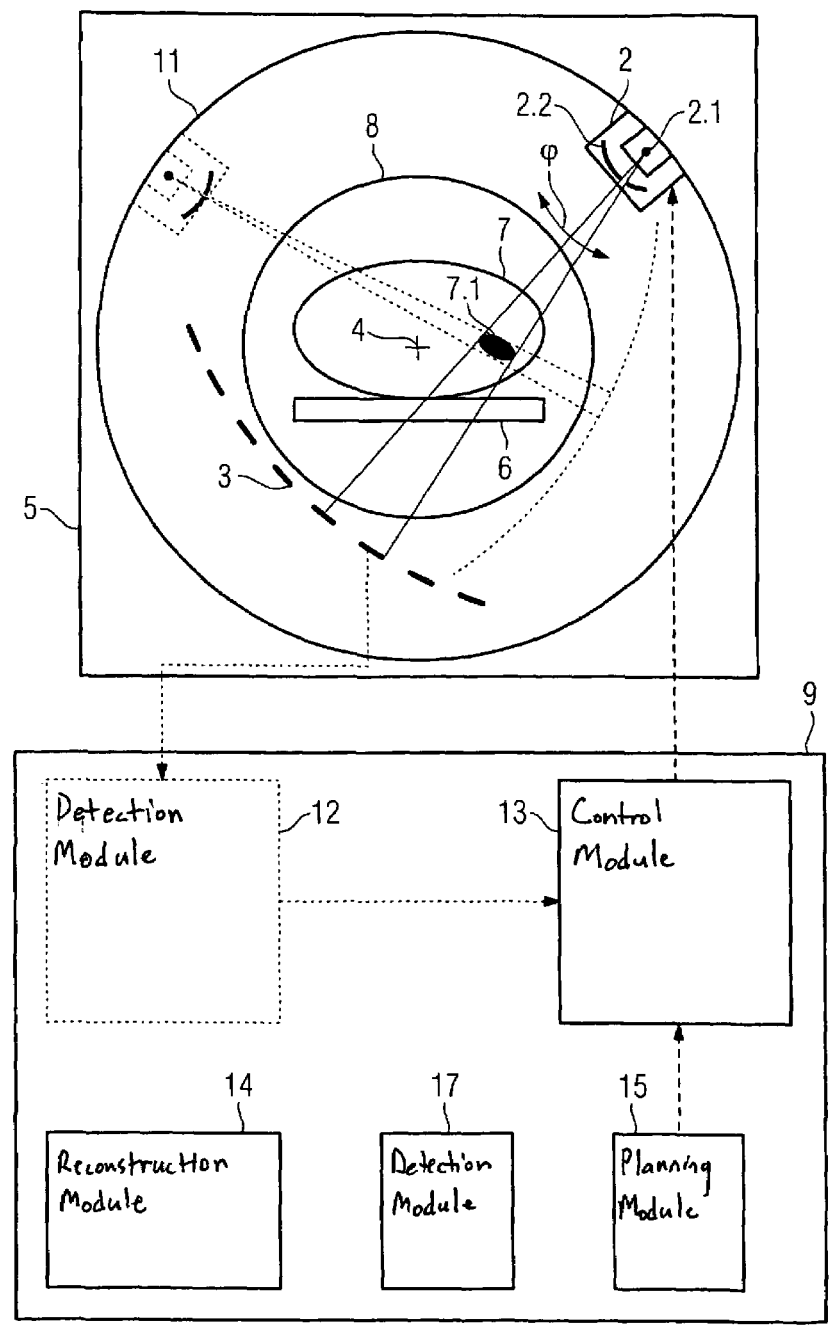
Figure 4:
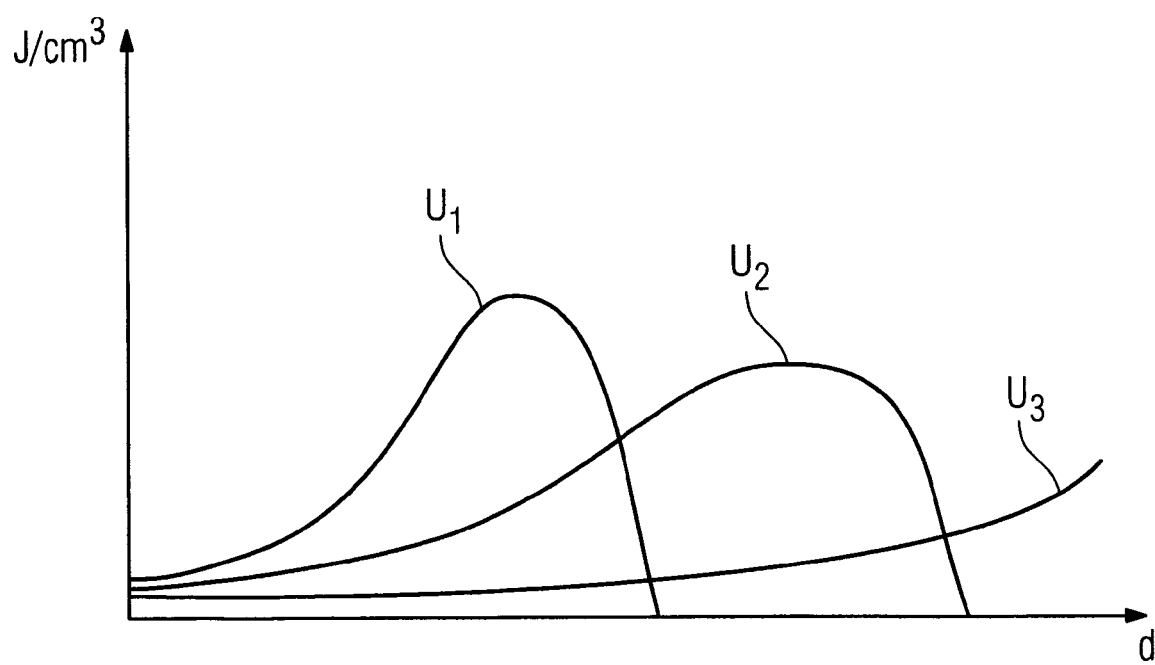

In detail:

FIG. 1 shows a system for producing CT image data records and for irradiating a tumor patient;

FIG. 2 shows the system in accordance with FIG. 1 in cross section, in the first operating mode;

FIG. 3 shows the system from FIG. 1 in cross section, in the second operating mode; and FIG. 4 shows an illustration of the different deposition of energy for various depths of penetration and different radiation energies.

DETAILED DESCRIPTION OF THE EXAMPLE EMBODIMENTS

FIG. 1 shows an inventive system 1 for producing CT image data records and irradiating a tumor patient, having a housing 5, in which a rotary frame or gantry is located on which an x-ray tube 2 and a detector 3 situated opposite are fastened. A patient 7 can be displaced through an opening 8 at the center of the rotary frame along a system axis 4 with the aid of a patient couch 6, which can be displaced longitudinally, into the area of the opening 8 and be both scanned and therapeutically irradiated with the same x-ray tube in the process without the need to be repositioned. The control, data collection and therapy planning are carried out by an arithmetic logic and control unit 9 that is connected to the irradiation system and the displaceable couch via a control and data line 10. The individual inventive method steps are carried out by the programs Prg1 to Prgn, this being implemented in the arithmetic logic unit 9.

In order to explain an example embodiment of the invention, FIG. 2 illustrates a cross section through the housing 5 of the combined system in a schematic fashion. Located in the housing 5 is the rotary frame 11 on which an x-ray tube 2 with a detector 3 situated opposite are arranged. The x-ray tube has a focal spot 2.1 or focus starting from which a ray fan 16 with a fan angle φ strikes the detector 3 situated opposite. This detector 3 can be a single row detector, but it is preferred to use a multirow detector.

The patient 7 is located on a patient table 6 that can be displaced along the system axis 4, a tumor 7.1 being illustrated here by way of example in the patient 7. Owing to the rotation of the x-ray tube 2 and the detector 3, it is possible by collecting the absorption values of the radiation striking the detector 3 in a way generally known to reconstruct a volume display of the patient 7. In order to display the rotation of the x-ray tube and detector, the same tube/detector is illustrated again in a different angular position with the aid of dotted lines. The reference symbols for this are provided with a prime.

Indicated schematically, in addition, in the lower area of FIG. 2 is the arithmetic logic unit 9 that in this first operating mode includes the detector module 12 for acquiring and collecting the detector data, and the control module 13 that executes the rotation and overall control of the system. In addition, the respective angular position of the x-ray/detector system in relation to the collected data is passed on via the data line between the module 13 and the module 12. Once all the data have been collected, they are transmitted to the reconstruction module 14 where the image reconstruction or reconstruction of the volume data of the patient takes place. In this operating mode, the system corresponds to a simple computer tomograph such as is known from the prior art.

After termination of the volume data reconstruction by the reconstruction module 14, the volume data can be transmitted to an automatic detection module 17 in which the position of a tumor 7.1 in the patient is determined on the basis of the volume data records. This position of the tumor is subsequently passed on together with the further volume data of the patient to the planning module 15 in which the automatic irradiation planning is carried out.

In the second operating mode of the this system, which is illustrated schematically in FIG. 3, the planning module 15 has carried out the calculation of the radiation therapy, and now passes the required data for control purposes on to the control module 13 that now carries out the irradiation of the patient 7 and, in particular, of the tumor 7.1.

As is to be seen in FIG. 3, this results in the production of a substantially more focused ray fan 16 that is always exactly aligned with the actual position of the tumor 7.1 in the patient 7 regardless of the direction of rotation of the gantry, and is also set with reference to its width in accordance with the projection as seen from the focus 2.1. It is also to be seen in FIG. 3 that the focal spot 2.1 is of substantially larger design than in FIG. 2, and so no premature wear of the anode can occur even when the latter is subjected to permanent loading in the x-ray tube 2 because of the higher dose rate.

Of course, in the case of this therapeutic irradiation different accelerating voltages can now be set as a function of the current angle of rotation of the x-ray tube. It is possible to insert an additional spectral filter of respectively varying thickness in the beam path in order to achieve the desired beam hardness of the x-ray beam 16. Again, it is possible to effect dose modulation by varying the tube current or varying the pulse width.

With regard to the change in radiation energy and the different energy depositions associated therewith as a function of the depth of penetration of the radiation, reference is made to the following FIG. 4. In this figure, the deposited energy per $cm^3$ is plotted against the depth of penetration d. The three illustrated graphs of the energy deposition for the different accelerating voltages $U_1$ to $U_3$ show, admittedly in a somewhat exaggerated illustration, how the depth of penetration varies with growing radiation energy, the energy deposited in the tissue, that is to say the therapeutically active dose, being applied at different layer depths such that it is also especially possible to output the therapeutic dose at respectively different depths of penetration by appropriately varying the accelerating voltage and thereby the energy distribution of the x-ray spectrum.

It is self evident that the abovenamed features of an embodiment of the invention can be used not only in the respectively specified combination, but also in other combinations or on their own without departing from the scope of the invention. Thus, at least one embodiment of the overall the invention exhibits a system for producing CT image data records and for irradiating a tumor patient that is provided with exactly one rotary frame for holding at least one x-ray tube and a radiation detector situated opposite, the x-ray tube being equipped with a diaphragm that can be adjusted dynamically during the rotation of the rotary frame. The system, in at least one embodiment, has a first operating mode for imaging in which during the revolution of the rotary frame the x-ray tube radiates a ray fan of constant fan angle onto the oppositely situated detector, and CT image data records are calculated from the measured data of the detector; and has a second operating mode for irradiation, in which at least one x-ray tube used for imaging in the first operating mode radiates an x-ray fan that varies with reference to alignment during the rotation of the rotary frame, is narrower perpendicular to the system axis, and remains aligned with the site of at least one tumor in the patient independently of the angular position of the rotary frame.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A system for producing CT image data records and for irradiating a patient, comprising:
   exactly one rotary frame for holding at least one radiation source, and at least one radiation detector situated opposite to move about a system axis;
   at least one x-ray tube as the at least one radiation source, including a diaphragm that is dynamically adjustable during rotation of the rotary frame;
   at least one detector including a multiplicity of detector elements, arranged in planar fashion, to measure radiation emanating from the x-ray tube; and
   an arithmetic logic and control unit, wherein in a first operating mode for imaging, during the revolution of the rotary frame the at least one x-ray tube radiates a ray fan of constant fan angle onto the oppositely situated detector, and CT image data records are calculated from the measured radiation of the detector, and
   in a second operating mode for irradiation, at least one x-ray tube, used for imaging radiates an x-ray fan that varies with reference to alignment during the rotation of the rotary frame, is relatively narrower perpendicular to the system axis than the ray fan of the first operating mode, and remains aligned with the site of at least one tumor in a patient independently of the angular position of the rotary frame, wherein during the irradiation, the patient has a means for sensitizing the at least one tumor to radiation, and a relatively smaller focal spot is present at the x-ray tube in the first operating mode, as compared to the second operating mode.

2. The system as claimed in claim 1, wherein during the irradiation, the patient has a contrast medium for improved display of the at least one tumor.

3. The system as claimed in claim 1, wherein the movement of the ray fan in the second operating mode is performed by continuous diaphragm adjustment.

4. The system as claimed in claim 3, wherein, in the second operating mode, the ray fan is also varied with reference to its width perpendicular to the system axis by a continuous diaphragm adjustment.

5. The system as claimed in claim 1, wherein, in the second operating mode, the ray fan is varied with reference to its width perpendicular to the system axis by a continuous diaphragm adjustment.

6. The system as claimed in claim 1, wherein, in the second operating mode, an accelerating voltage is varied during a rotation in order to match the depth of penetration and deposition of energy to the position of the at least one tumor in the patient.

7. The system as claimed in claim 1, wherein the x-ray tube includes at least one spectral pre-filter that, when appropriate during operation, is introduceable into the beam path in order to change the x-ray spectrum used.

8. The system as claimed in claim 1, wherein, in the second operating mode, the dose rate is varied during a rotation in order to load healthy tissue less.

9. The system as claimed in claim 1, wherein a second irradiation source is additionally fitted on the rotary frame.

10. The system as claimed in claim 9, wherein the second irradiation source is an x-ray source, and wherein the second irradiation source has a variable diaphragm control that, when appropriate, is alignable for simultaneously irradiating a further tumor.

11. The system as claimed in claim 1, wherein the rotary frame additionally includes at least one of a PET and SPECT detector.

12. The system as claimed in claim 1, wherein an operating program product is present within the system and executed by the system, wherein the operating program product includes instructions for moving the patient relative to the rotary frame sequentially in a direction of the system axis, performing image evaluation and automatic detection of the position of the at least one tumor taking place in the first operating mode at each sequential position of the system axis, subsequently carrying out an automatic irradiation plan over the measured section with the aid of the measured structure of the patient, and thereupon in the second operating mode irridating the at least one tumor of the patient with the aid of the irradiation plan.

13. The system as claimed in claim 1, wherein an operating program product is present within the system and executed by the system, wherein the operating program product includes instructions for moving in the first operating mode the patient continuously in a direction of the system axis relative to the rotary frame and carrying out a complete spiral scan, performing image evaluation and automatic detection of the position of the at least one tumor taking place, subsequently carrying out an automatic irradiation plan with the aid of the measured structure of the patient, and thereupon in the second operating mode continuously irradiating the at least one tumor with the aid of the irradiation plan.

14. The system as claimed in claim 1, wherein an operating program product is present within the system and executed by the system, wherein the operating program product includes instructions for measuring the absorption of radiation on the detector during therapeutic use of this radiation in the second operating mode, and detecting a movement of the tumor that may be present.

15. The system as claimed in claim 14, wherein the operating program product further includes instructions for using the currently detected movement of the tumor in order to correct the diaphragm setting and/or irradiation parameters.

* * * * *